United States Patent [19]

Gryaznov et al.

[11] 4,388,479
[45] Jun. 14, 1983

[54] PROCESS FOR PRODUCING C$_4$-C$_{10}$ ETHYLENE ALCOHOLS

[76] Inventors: Vladimir M. Gryaznov, Lomonosovsky prospekt, 14, kv. 504; Andrei N. Karavanov, ulitsa Fabritsiusa, 20, kv. 29; Tamara M. Belosljudova, ulitsa Konenkova, 11, kv. 60, all of Moscow; Anatoly V. Ermolaev, poselok Shvarts, ulitsa Mendeleeva 7, kv. 54, Tulskaya oblast; Anatoly P. Maganjuk, Yasenevo, 9 mikroraion, 73, kv. 540; Irina K. Sarycheva, ulita Baumanskaya, 62, kv. 85, both of Moscow, all of U.S.S.R.

[21] Appl. No.: 252,307

[22] Filed: Apr. 9, 1981

[51] Int. Cl.$^3$ ............................................. C07C 29/17
[52] U.S. Cl. .................................... 568/828; 568/857; 568/903
[58] Field of Search ........................ 568/903, 857, 828

Primary Examiner—Robert Gerstl
Attorney, Agent, or Firm—Myron Greenspan

[57] ABSTRACT

The process for producing C$_4$-C$_{10}$ ethylene alcohols of the formula:

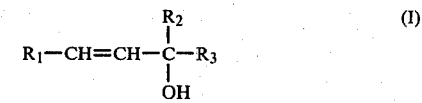

wherein
(a) R$_1$ is —CH$_2$OH, R$_2$=R$_3$=—H;
(b) R$_1$ is —H, R$_2$=—CH$_3$, R$_3$=—CH$_3$ or —C$_6$H$_{11}$ comprises hydrogenation of acetylene alcohols of the formula:

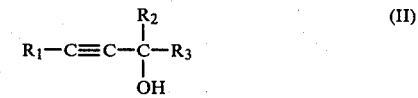

wherein
(a) R$_1$ is CH$_2$OH, R$_2$=R$_3$=—H;
(b) R$_1$ is —H, R$_2$ is —CH$_3$, R$_3$ is —CH$_3$ or —C$_6$H$_{11}$, in the form of technical products in the liquid phase on a membrane catalyst made of an alloy consisting of palladium and ruthenium at a mass ratio therebetween of 90-94:10-6 respectively. Hydrogenation of said alcohols is effected by means of hydrogen diffusing through a membrane catalyst at a temperature of from 60° to 180° C. under atmospheric pressure of hydrogen. The process is simple in its scheme and the equipment employed. It avoids losses of noble metals of the catalyst and makes it possible to obtain the desired products in a yield of up to 99.2% of the theoretical, as well as to use both pure and technical hydrogen. It can be effected both discontinuously and continuously. The catalyst employed retains its activity for a long time and can be easily regenerated.

4 Claims, No Drawings

PROCESS FOR PRODUCING $C_4$-$C_{10}$ ETHYLENE ALCOHOLS

FIELD OF THE INVENTION

The present invention relates to processes for producing ethylene compounds and, more specifically, to processes for producing $C_4$–$C_{10}$ ethylene alcohols. These alcohols comprise valuable intermediate products for fine organic synthesis and can be useful in the production of vitamins and cosmetics.

BACKGROUND OF THE INVENTION

Known in the art is a process (cf. USSR Inventor's Certificate No. 311887 Cl. C 07 C 31/20, 1971) for producing ethylene alcohol namely 2-butenediol-1,4 by hydrogenation of 2-butynediol-1,4 with hydrogen in an organic solvent medium in the presence of oxalic acid on a catalyst of a mixture of palladium black and black of a metal of the platinum group (except platinum per se). In this process, wherein use is made of palladium black and ruthenium black, the process selectivity at a temperature of 20° C. is equal, relative to 2-butenediol-1,4, to 96% at full conversion; stereospecificity relative to cis-2-butenediol-1,4 is equal to 97%.

This prior art process has disadvantages residing in the following:

(1) the necessity of using a pure starting alcohol and pure hydrogen;

(2) hydrogenation is conducted in an organic solvent medium in the presence of oxalic acid, thus adding to the production costs;

(3) mechanical strength of the catalyst in the form of a metal black is insufficient, wherefore separation of the catalyst from the reaction mixture is hindered;

(4) difficulties are encountered in regeneration of the catalyst after lowering of its activity: thermal treatment cannot be applied due to sintering of the black particles, wherefore in this case regeneration of the catalyst should be preferably effected by its dissolution to recover noble metals and subsequently prepare a fresh portion of the black. However, this regeneration scheme is laborious.

In another prior art process (cf. FRG Pat. No. 2,431,929 Cl. C 07 C 33/02, 1976; U.S. Pat. No. 4,001,344 Cl. 260-635, 1977; British Pat. No. 1,504,187 Cl. B1E, 1978) 2-butenediol-1,4 is produced by hydrogenation, with hydrogen, of a technical product, namely a 30% aqueous solution of 2-butynediol-1,4 on a catalyst containing 0.05 to 2% by mass of palladium, 0.05 to 1% by mass of zinc and cadmium supported by γ-alumina at a temperature within the range of from 60° to 75° C. under a hydrogen pressure of from 1 to 16 atm. The yield of 2-butene-1,4-diol is 88 to 92.5% of the theoretical. The above-indicated starting technical product is prepared by a conventional Reppe process using acetylene and an aqueous solution of formaldehyde in the presence of copper acetylenide.

A disadvantage of this prior art process for producing 2-butenediol-1,4 resides in the formation of resinous products in an amount of from 7.5 to 12% by mass. Furthermore, other disadvantages are associated with a relatively low yield of the desired product, the necessity of its separation from the catalyst by filtration and accompanying losses of the noble metal (palladium), difficulties of regeneration of the catalyst after lowering of its activity (the regeneration comprises the recovery of the noble metal from the spent catalyst and the preparation of a fresh portion of the catalyst). The obligatory stage of separation of the desired product from the catalyst and considerable labor-consumption in the regeneration stage complicate the overall process.

In the process disclosed in British Pat. No. 888,999 Cl I/I/A31B1, 1962, acetylene alcohols in the form of commercial products, e.g. commercial 2,6-dimethylocten-2-in-7-ol-6 (dehydrolinalool) and commercial 2-methylbutyn-3-ol-2 (dimethylethynylcarbinol) are selectively hydrogenated with hydrogen into corresponding ethylene alcohols under atmospheric pressure of hydrogen in a medium of a solvent or without on a catalyst containing up to 20% by mass of palladium and 0.1 to 20% by mass of lead deposited on barium sulphate, calcium carbonate or barium carbonate, activated coal or magnesia at a temperature within the range of from 10° to 75° C. The hydrogenation process is conducted discontinuously. Separation of the desired product from the catalyst is effected by vacuum distillation. The yield of 2,6-dimethyloctadien-2,7-ol-6 (linalool) is 90.5%, that of 2-methylbuten-3-ol-2 (dimethylvinylcarbinol) is 97% as calculated for the starting acetylene alcohol.

The discontinuous scheme of the hydrogenation process and the use of vacuum distillation substantially increase the process duration. The vacuum distillation also necessitates the use of expensive process equipment and lowers the yield of the desired products.

It should be noted that the liquid-phase hydrogenation of acetylene alcohols under continuous flow-through conditions on the catalysts employed in all the above-described prior art processes is impossible due to unavoidable high losses of noble metals of the catalyst. Furthermore, a common disadvantage of the above-mentioned prior art processes is the difficult regeneration of catalysts on carriers and catalysts in the form of a noble metal black. Such regeneration contemplates dissolution of noble metals in a mixture of nitric acid, recovery of chlorides of noble metals and preparation of a fresh portion of the catalyst. All these operations take a long time and necessitate the use of special sophisticated process equipment.

BRIEF SUMMARY OF THE INVENTION

It is an object of the present invention to provide a process for producing ethylene $C_4$–$C_{10}$ alcohols which makes it possible to eliminate losses of noble metal catalyst components.

It is another object of the present invention to provide a process which makes it possible to increase the yield of the final products.

It is a further object of the present invention to provide a process which can be carried out both continuously and discontinuously.

It is another object of the present invention to avoid the stage of separating of the final product from the catalyst and, thereby, intensification of the overall process.

It is a further object of the present invention to simplify regeneration of the catalyst employed in the hydrogenation process.

It is another object of the present invention to provide a process which makes it possible to use both pure and technical-grade hydrogen for the purpose of hydrogenation.

These objects are accomplished by a process for producing $C_4$–$C_{10}$ ethylene alcohols of the formula:

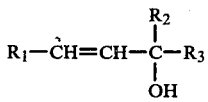
(I)

wherein
(a) $R_1$ is $-CH_2OH$, $R_2=R_3=-H$,
(b) $R_1$ is H, $R_2=-CH_3$, $R_3=-CH_3$ or $C_6H_{11}$
which comprises hydrogenation, with hydrogen, of acetylene alcohols of the formula:

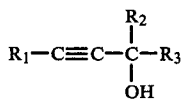
(II)

wherein
(a) $R_1$ is $-CH_2OH$, $R_2=R_3=H$,
(b) $R_1$ is H, $R_2$ is $-CH_3$, $R_3$ is $CH_3$ or $-C_6H_{11}$
in the form of technical products in the liquid phase on a palladium-containing catalyst under atmospheric pressure of hydrogen. In accordance with the present invention the hydrogenation is carried out at a temperature within the range of from 60° to 180° C. on a membrane catalyst made of an alloy containing, in addition to palladium, also ruthenium at a mass ratio therebetween of 90-94:10-6 respectively using hydrogen diffusing through the membrane catalyst.

The process according to the present invention has the following advantages over the prior art processes:

(1) the use of a solid membrane catalyst comprising a structural element of a reactor eliminates losses of noble metals of the catalyst;

(2) the use of a membrane catalyst of a palladium-ruthenium alloy makes it possible to hydrogenate commercial acetylene alcohols with higher yields of ethylene alcohols compared to the prior art processes—up to 99.2% of the theoretical yield;

(3) the use of a membrane catalyst makes it possible to carry out hydrogenation of acetylene alcohols under conditions of continuous flow, thus intensifying the process on the whole in comparison with the prior art processes;

(4) production of ethylene alcohol is intensified due to elimination of vacuum distillation and filtration from the process scheme which in the prior art processes are indispensible for the separation of the desired products from the catalyst;

(5) regeneration of the membrane catalyst is effected in a substantially simpler manner than regeneration of catalysts supported on carriers or metal black catalysts;

(6) the use of a membrane catalyst makes it possible to use non-purified technical hydrogen, since it becomes purified during its diffusion through the membrane catalyst.

As mentioned hereinbefore, the membrane catalyst employed in the process according to the present invention consists of an alloy of 90-94% by mass of palladium with 6 to 10% by mass of ruthenium. At a content of ruthenium below 6% by mass of the alloy becomes brittle in an atmosphere of hydrogen. At a content of ruthenium of up to 10% by mass its mechanical strength is increased. Thus, the tensile strength is increased from 18.8 kgf/mm² for pure palladium to 46 kgf/mm² for an alloy with a ruthenium content of 9.21% by mass. Alloys containing above 10% by mass of ruthenium have too low a permeability for hydrogen (thus, upon increasing the content of ruthenium in the alloy of from 10 to 12% by mass, hydrogen permeability is lowered by 2 times). The highest hydrogen permeability in combination with a high mechanical strength and plasticity is inherent only in the alloys containing ruthenium in an amount of from 6 to 10% by mass. Therefore, the use of palladium alloys with a content of ruthenium below 6% and above 10% by mass as a hydrogen-permeable catalyst is undesirable.

DETAILED DESCRIPTION OF THE INVENTION

The membrane catalyst according to the present invention comprises a 20-100 μm-thick foil or a thin-wall tube shaped as a helix with a wall thickness of from 50 to 200 μm made of the alloy of the above-specified composition. At one side of the foil or outside the tube there is the starting acetylene alcohol in the form of a technical product which is supplied either continuously or discontinuously, whereas along the other side of the foil or inside the tube, pure or non-purified technical hydrogen is passed continuously. This hydrogen diffuses through the foil or tube wall towards the opposite surface contacting the compound being hydrogenated. The hydrogenation process is carried out at a temperature within the range of from 60° to 180° C. under atmospheric pressure of hydrogen either discontinuously or continuously. The analysis of the catalyzate withdrawn from the reactor is effected by gas-liquid chromatography.

As mentioned hereinbefore, the starting materials—acetylene alcohols—are used in the process according to the present invention as technical products. Said technical products are prepared in a conventional manner. Thus, a technical product comprising a 30-35% aqueous solution of 2-butyndiol-1,4 is prepared by the Reppe method from acetylene and an aqueous solution of formaldehyde in the presence of copper acetylenide. Technical 2-methylbutyn-3-ol-2 (dimethylethynylcarbinol) and 2,6-dimethylocten-2-in-7-ol-6 (dehydrolinalool) are prepared by known methods through ethynylation of acetone and 2-methylhepten-2-on-6 respectively. In the resulting commercial acetylene alcohols the content of the starting carbonyl compounds is varied, as a rule, within the range of from 1.5 to 7% by mass.

It should be noted that the membrane catalyst made of an alloy consisting of 90-94% by mass of palladium and 6 to 10% by mass of ruthenium retains its activity without regeneration under the process conditions in hydrogenation of 2-butynediol-1,4 for 30 hours, in hydrogenation of technical dehydrolinalool-for more than 400 hours.

Regeneration of the membrane catalyst is effected directly in a hydrogenation reactor (without discharge of the catalyst) in a current of dry air at a temperature of 400° C. for one hour, followed by treatment with hydrogen at the same temperature for one hour. After such regeneration the catalyst activity is fully restored. This regeneration method is not laborious and features a simple process scheme.

For a better understanding of the present invention, some specific examples are given hereinbelow by way of illustration. Unless otherwise specified, all yields of the products in the Examples are expressed in percent by mass.

EXAMPLE 1

The hydrogenation process is conducted in a flow-type reactor consisting of two chambers separated from each other by means of a membrane catalyst made as a foil of an alloy consisting of 90% by mass of palladium and 10% by mass of ruthenium. The visible surface area of the membrane catalyst is 420 cm$^2$, thickness 20 μm. Into one of the chambers hydrogen is continuously fed under a pressure of 1 atm, while through the other one technical 2-butynediol-1,4 is continuously passed in the form of its 30% aqueous solution containing formaldehyde in an amount of 1.5% and small amounts of formic acid and propargyl alcohol at a rate of 33 ml/hr. The hydrogenation is conducted at a temperature of 60° C.

The yield of 2-butenediol-1,4 is equal to 98.6% of the theoretical value (stereoselectivity relative to cis-2-butenediol-1,4 is equal to 93.8%), that of butanediol-1,4 is 0.4%, resinous substances—below 1%. The amount of the unreacted 2-butyndiol-1,4 is less than 0.1% of the starting value. The catalyst productivity is 255 g (2.9 moles) of cis-2-butenediol-1,4 from 1 m$^2$ of the catalyst per hour.

EXAMPLE 2

Into a reaction vessel with technical 2-butynediol-1,4 (the composition of the commercial product is similar to that described in Example 1 hereinabove) a thin-wall tube in the shape of a coil made of an alloy of 94% by mass of palladium and 6% by mass of ruthenium is placed. The tube has a visible outer surface area of 30 cm$^2$, an outside diameter of 1 mm and a wall thickness of 100 μm. The temperature in the reaction vessel is elevated to 90° C., whereafter technical hydrogen containing 5% by volume of air is fed into the tube under a pressure of 1 atm. After absorption of 1 mole of hydrogen per 1 mole of 2-butynediol-1,4 there is obtained 2-butenediol-1,4 with a yield of 95.6% of the theoretical value (stereoselectivity relative to cis-2-butenediol-1,4 is equal to 96.2%), butanediol-1,4—with a yield of 1.2%, resinous products—with a yield of 3.2%. The amount of the unreacted 2-butynediol-1,4 is less than 0.1% of the initial value. The catalyst productivity is 200 g (2.3 moles) of cis-butenediol-1,4 from 1 m$^2$ per hour.

EXAMPLE 3

Technical 2-butynediol-1,4 (the composition of the technical product is similar to that described in Example 1) is subjected to hydrogenation on a membrane catalyst in the form of a foil of an alloy consisting of 92% by mass of palladium and 8% by mass of ruthenium. The foil thickness is 100 μm, visible surface area 10 cm$^2$. The hydrogenation process is conducted discontinuously at a temperature of 72° C. under a hydrogen pressure of 1 atm.

The yield of 2-butenediol-1,4 is equal to 95.5% of the theoretical (stereoselectivity relative to cis-2-butenediol-1,4 is equal to 96.8%), that of butanediol-1,4 is 1.5%, and the yield of resinous substances is 2.0%. The amount of unreacted 2-butynediol-1,4 is 1.0% of the initial value. The catalyst productivity is 106 g (1.2 mol) of cis-2-butenediol-1,2 per hour from 1 m$^2$.

EXAMPLE 4

Commercial 2-methylbutyn-3-ol-2 (dimethylethynylcarbinol) containing 5% by mass of acetone is hydrogenated in a flowtype reactor similar to that described in Example 1 on a membrane catalyst shaped as a foil of an alloy consisting of 90% by mass of palladium with 10% by mass of ruthenium. The visible surface area of the catalyst is 22 cm$^2$, the foil thickness is 30 μm. The hydrogenation process is carried out at a temperature of 90° C. at an alcohol supply rate of 3 ml/hr.

The yield of 2-methyl-butene-3-ol-2 (dimethylvinylcarbinol) is 99.2% of the theoretical; the yield of tert.a-myl alcohol is 0.7%. The amount of unreacted dimethylethynylcarbinol is less than 0.1% of the initial value. The catalyst productivity is 1.9 kg (13.8 moles) of dimethylvinylcarbinol from 1 m$^2$ per hour.

EXAMPLE 5

Technical 2,6-dimethylocten-2-in-7-ol-6 (dehydrolinalool) containing 6.5% by mass of 2-methylhepten-2-on-6 is hydrogenated as described in Example 2 on a membrane catalyst of an alloy of 94% by mass of palladium with 6% by mass of ruthenium at a temperature of 90° C.

The yield of 2,6-dimethyloctadien-2,7-ol-6 (linalool) is 99.0% of the theoretical value; that of 2,6-dimethylocten-2-ol-6 (dihydrolinalool) is 0.9%. The amount of the unreacted dehydrolinalool is less than 0.1% of the initial value. The catalyst productivity is 620 g (4.0 moles) of linalool from 1 m$^2$ per hour.

EXAMPLE 6

Technical dehydrolinalool having the same composition as in the foregoing Example 5 is hydrogenated in a flow-type reactor described in Example 1 on a membrane catalyst made as a foil from an alloy consisting of 94% by mass of palladium and 6% by mass of ruthenium. The visible surface area of the catalyst is 360 cm$^2$, the foil thickness is 50 μm. The hydrogenation process is carried out at a temperature of 180° C. at a supply rate of dehydrolinalool of 145 ml/hr.

The yield of linalool is 95.2% of the theoretical value (the selectivity relative to linalool is 97%), the yield of dihydrolinalool is 3.2%. The amount of the unreacted dehydrolinalool is 1.6% of the initial value. The catalyst productivity is 3.46 kg (22.5 moles) of linalool from 1 m$^2$ per hour.

What is claimed is:

1. A process for producing C$_4$-C$_{10}$ ethylene alcohols of the formula:

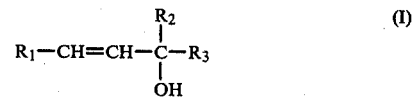

(I)

wherein
(a) R$_1$ is —CH$_2$OH, R$_2$=R$_3$=—H;
(b) R$_1$ is —H, R$_2$ is —CH$_3$, R$_3$ is a radical selected from the group consisting of —CH$_3$ and —C$_6$H$_{11}$ comprising hydrogenation of acetylene alcohols of the formula:

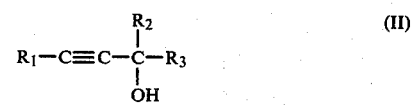

(II)

wherein
(a) R$_1$ is —CH$_2$OH, R$_2$=R$_3$=—H;

(b) $R_1$ is —H, $R_2$ is —$CH_3$ and $R_3$ is a radical selected from the group consisting of —$CH_3$ and —$C_6H_{11}$ in the form of technical products in the liquid phase on a membrane catalyst made of an alloy consisting of palladium and ruthenium at a mass ratio therebetween of 90–94:10–6 respectively; hydrogenation of said alcohols is effected by means of hydrogen diffusing through the membrane catalyst at a temperature of from 60° to 180° C. and atmospheric pressure of hydrogen.

2. The process of claim 1, wherein the catalyst is in the form of a foil or a thin-walled tube having a wall thickness varying from 20 to 200 microns.

3. The process of claim 1, wherein the catalyst is regenerated directly in a hydrogenation reactor in a current of dry air at a temperature of about 400° C. for about one hour followed by treatment with hydrogen at about 400° C. for about one hour.

4. The process of claim 1, wherein the hydrogenation is accomplished with non-purified technical hydrogen.

* * * * *